United States Patent
Randolph et al.

[11] Patent Number: 5,775,327
[45] Date of Patent: Jul. 7, 1998

[54] GUIDING CATHETER FOR THE CORONARY SINUS

[75] Inventors: Yvonne Randolph, Morgan Hill; Duane Dickens, San Clemente, both of Calif.

[73] Assignee: Cardima, Inc., Fremont, Calif.

[21] Appl. No.: 858,297

[22] Filed: May 19, 1997

Related U.S. Application Data

[63] Continuation of Ser. No. 484,715, Jun. 7, 1995, abandoned.

[51] Int. Cl.⁶ .......................... A61B 5/04; A61M 29/00
[52] U.S. Cl. .......................... 128/642; 128/657; 128/772; 606/41; 604/96; 604/282
[58] Field of Search .................. 128/642, 657, 128/658, 772; 604/96, 280–282; 606/41

[56] References Cited

U.S. PATENT DOCUMENTS

| | | | |
|---|---|---|---|
| 5,016,640 | 5/1991 | Ruiz | 128/658 |
| 5,045,072 | 9/1991 | Castillo et al. | 604/280 |
| 5,195,990 | 3/1993 | Weldon | 604/281 |
| 5,306,262 | 4/1994 | Weldon | 604/281 |
| 5,306,263 | 4/1994 | Voda | 604/281 |
| 5,318,032 | 6/1994 | Lonsbury et al. | 128/658 |
| 5,423,772 | 6/1995 | Lurie et al. | 604/282 |
| 5,488,960 | 2/1996 | Toner | 128/772 |
| 5,499,973 | 3/1996 | Saab | 604/96 |
| 5,509,411 | 4/1996 | Littman et al. | 128/642 |

FOREIGN PATENT DOCUMENTS

| | | |
|---|---|---|
| WO 9108014 A | 6/1991 | WIPO |
| WO 9215356A | 9/1992 | WIPO |

*Primary Examiner*—Jeffrey R. Jastrzab
*Attorney, Agent, or Firm*—Heller Ehrman White & McAuliffe

[57] ABSTRACT

A guiding catheter for delivery of intravascular devices to a patient's coronary sinus. The guiding catheter has a relatively stiff proximal section and a relatively flexible distal section, the latter being about 1 to about 6 inches in length and being configured to subselect a branch cardiac vein leading to the coronary sinus. The guiding catheter is particularly suitable for delivering an intravascular device for sensing electrical activity into a cardiac vein to detect such activity from within the blood vessel.

16 Claims, 4 Drawing Sheets

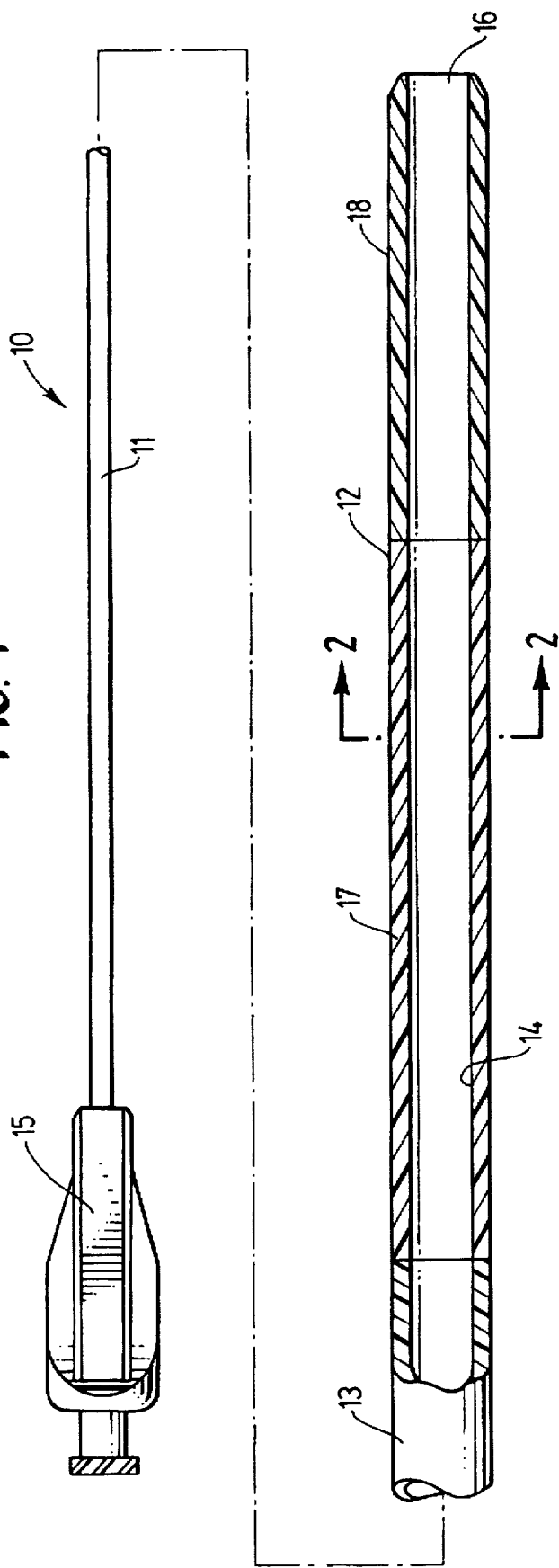

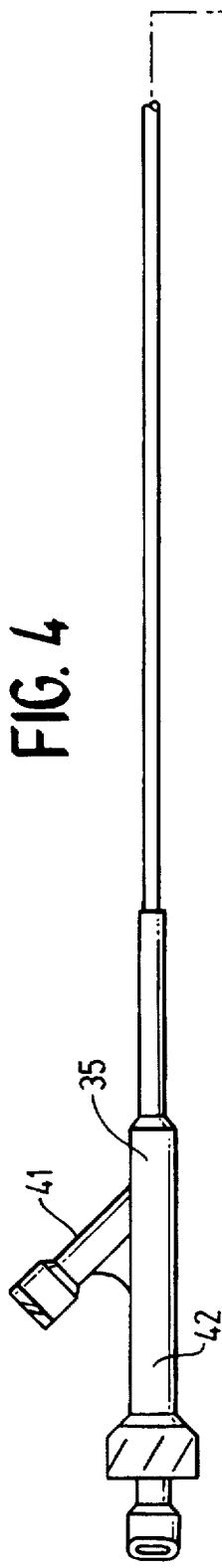
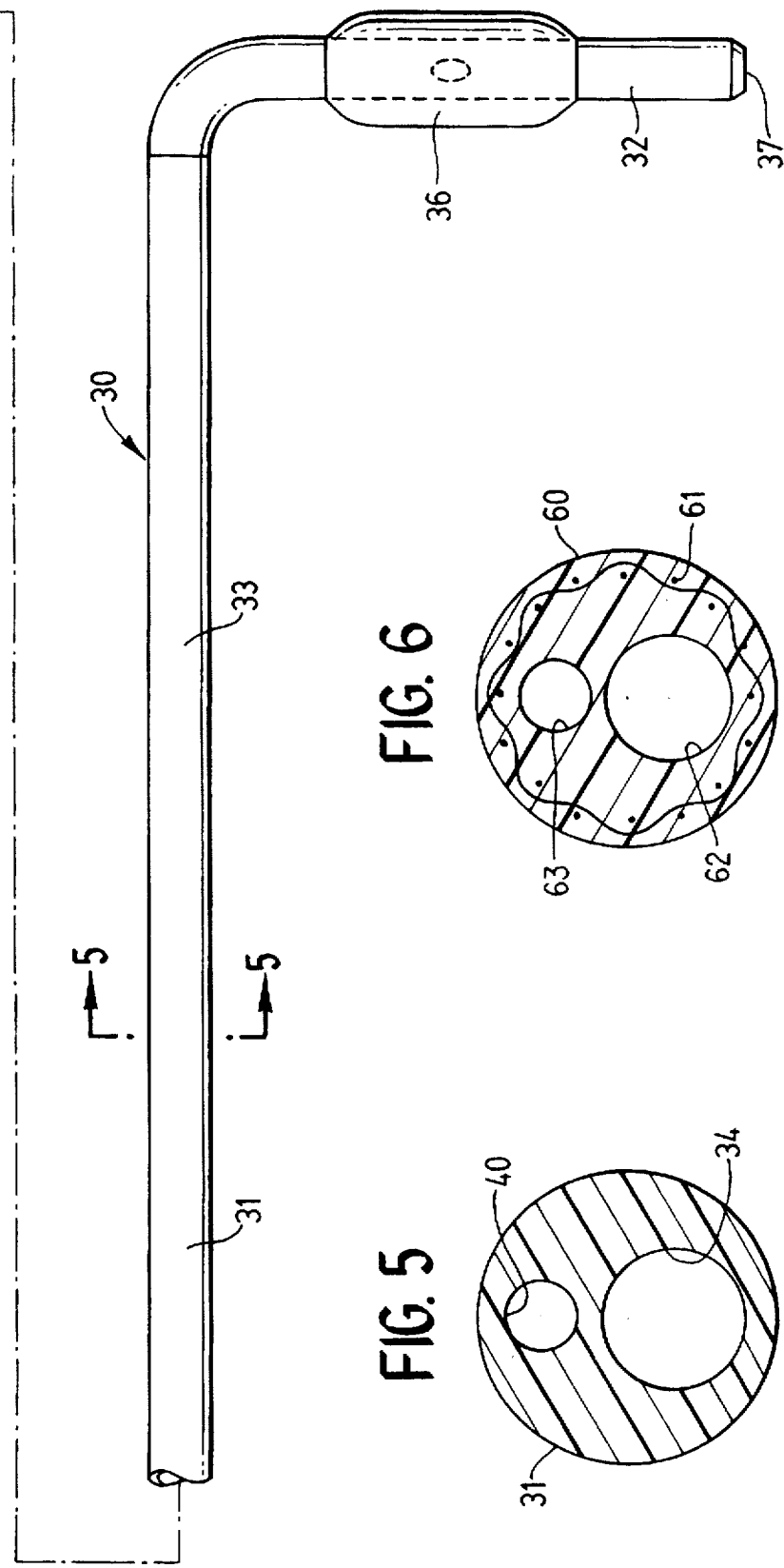
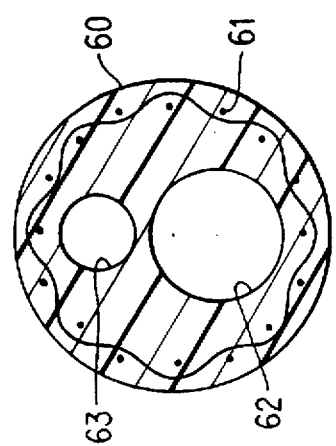
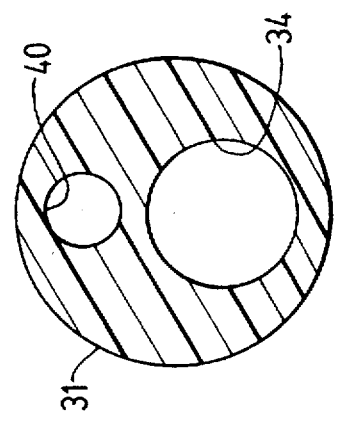
FIG. 4
FIG. 5
FIG. 6

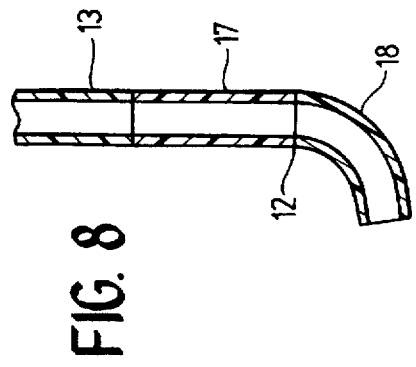
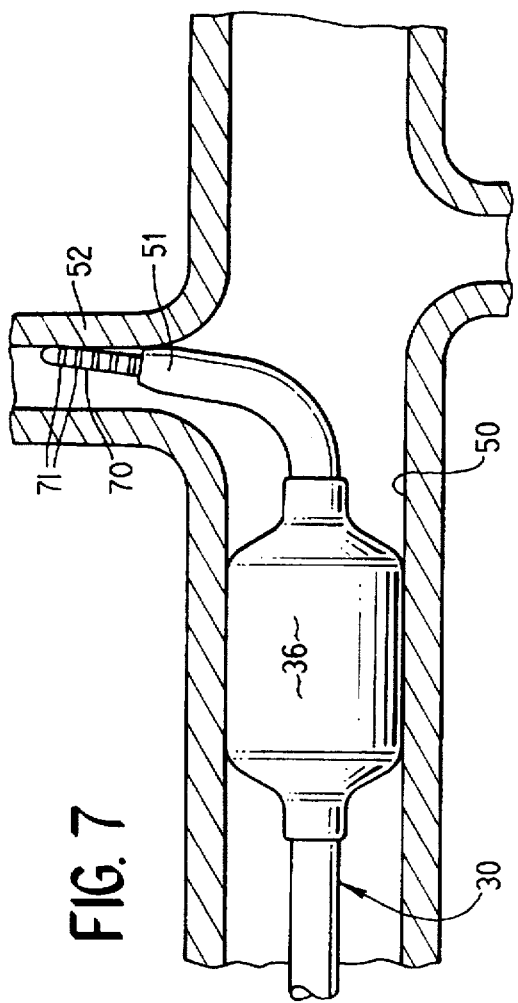
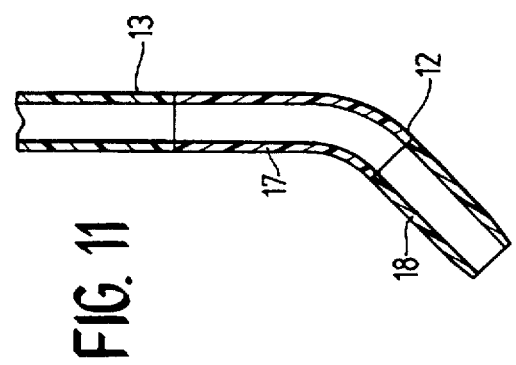
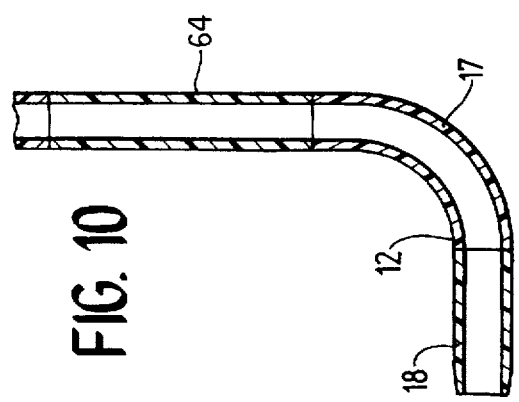
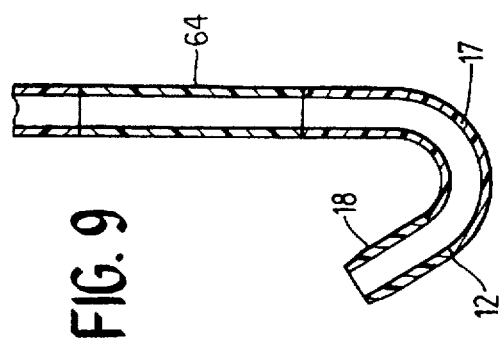

GUIDING CATHETER FOR THE CORONARY SINUS

This is a continuation of application Ser. No. 08/484,715, which was filed on Jun. 7, 1995 now abandoned.

BACKGROUND OF THE INVENTION

This invention generally relates to a guiding catheter for the direction of an intravascular device into a patient's coronary sinus and particularly to the direction of a mapping device into a cardiac vein draining into the coronary sinus for detecting electrical activity or signals causing or involved with arrhythmia from within the cardiac vein.

One of the most frequently used treatment modalities for arrhythmia is to destroy or damage heart tissue which causes the arrhythmia or involved with the arrhythmia by suitably heating the tissue, e.g. applying a laser beam or high frequency electrical energy (RF or microwave).

To be effective, the location of the tissue site causing or involved with the arrhythmia must be accurately determined in order to be able to contact a heart surface adjacent to the desired location with a tissue device. A major problem of ablating the site of the origin of the signals or a conductive pathway with commercially available devices is that an excessive amount of good tissue is very frequently damaged or destroyed along with the arrhythmogenic site to ensure that the arrhythmia does not return. For example, the average arrhythmogenic site consists of about 1.4 cm$^2$ of endocardial tissue, whereas a re-entrant site might be much larger. RF ablation techniques with commercially available devices produce lesions about 0.5 cm$^2$ in diameter, so that it may be necessary to form several overlapping lesions in the region in order to completely ablate the area of interest and termination of the arrhythmia. If the arrhythmogenic or re-entrant site has not been accurately mapped, much good tissue surrounding the site will be unnecessarily damaged or destroyed to ensure termination of the arrhythmia.

A variety of methods have been used to detect electrical activity within a patient's heart to facilitate the mapping of electrical activity causing the arrhythmia. A number of U.S. Patents describe the use of elongated intravascular signal sensing devices which are advanced through the patient's vasculature until the distal portions of the sensing devices are disposed within a patient's heart chamber with one or more electrodes on the distal portion of the sensing device in contact with the endocardial lining. While this procedure is widely used, it does not always allow the site of arrhythmogenic signals to be accurately determined and frequently results in unnecessary damage to heart tissue which may already be in jeopardy.

Copending application Ser. No. 08/188,619, filed Jan. 27, 1994 now U.S. Pat. No. 5,509,041 entitled INTRAVASCULAR SENSING DEVICE describes intravascular devices which can be advanced into a patient's coronary artery or cardiac vein where the device is used to detect electrical activity of the patient's heart.

While there are commercially available guiding catheters suitable for directing a variety of intravascular devices into a patient's coronary arteries, there are no devices available which allow for the rapid advancement of an intravascular device into a patient's coronary sinus and particularly into a cardiac vein draining into the coronary sinus.

SUMMARY OF THE INVENTION

The present invention is directed to a guiding catheter which is configured to be advanced through the patient's peripheral vascular system, through the right atrium and into the coronary sinus through the coronary sinus ostium. Within the coronary sinus the distal end of the guiding catheter is used to subselect and enter a branch vein leading toward the coronary sinus.

The guiding catheter of the invention has a relatively stiff proximal shaft section and a relatively flexible distal shaft section which is at least in part shaped or is shapeable to a shape suitable for advancement within the patient's coronary sinus and particularly a branch vein thereof. The distal shaft section preferably has a proximal portion which has a flexibility greater than that of the proximal shaft section and a distal portion which has a flexibility greater than that of the proximal portion of the distal shaft section. An inner lumen extends within the catheter shaft to and in fluid communication with a port in the distal end thereof. An intermediate shaft section may be disposed between the proximal and distal shaft sections and have a flexibility intermediate that of the proximal and distal shaft sections.

The proximal shaft section is preferably formed of polymer material having a durometer hardness of about 60D to about 90D (Shore), the intermediate section a polymer material having a durometer hardness of about 30D to about 60D (Shore) and the distal shaft section of a polymer material having a durometer hardness of about 80A to about 20D (Shore). A suitable material for the proximal shaft section is Pebax 7233 (available from Atochem), a suitable material for the proximal portion of the distal shaft section is Pebax 5533 (also available from Atochem) and a suitable material for the distal portion of the distal shaft section is Tecothane (available from Thermedics, Inc.

The length of the distal shaft section is about 2 to about 7 cm, preferably about 3 to about 6 cm to ensure that the distal end of the catheter shaft seats well into the desired vein branching off from the coronary sinus. The length of the intermediate shaft section is about 1 to about 8 centimeters. The overall length of the catheter shaft is about 25 to about 75 cm.

In one presently preferred procedure the catheter is introduced into the patient's venous system, e.g the femoral vein, by conventional Seldinger techniques and advanced through the patient's vasculature into the right atrium. The proximal end of the catheter shaft extending out of the patient is torqued to guide the distal end of the catheter through the coronary sinus ostium into the coronary sinus. With the distal end of the catheter within the coronary sinus, the catheter is advanced and further torqued to direct its distal end into a desired branch vein which drains into the coronary sinus. Alternatively, the catheter can be advanced over a guidewire which is slidably disposed at the inner lumen thereof with the distal extremity of the guidewire being disposed within the desired location within the patient's coronary sinus or branch vein. However, in this latter instance the catheter shaft need not be torquable but it must have sufficient pushability to be advanced over the guidewire.

When the guiding catheter of the present invention is properly positioned within the patient's coronary sinus with its distal extremity seated within the desired branch vein which drains into the coronary sinus, an intravascular device having sensing electrodes on the distal extremity thereof may be advanced through the inner lumen of the guiding catheter into the branch vein. The intravascular device is advanced through the branch vein until the sensing electrodes on its distal end are positioned at a desired location within a branch vein beyond the distal end of the guiding

3 catheter. Electrical activity, such as electrical activity causing or involved with arrhythmia, may be detected by the sensing electrodes and the activity sensed is converted to signals which are used to develop a visual representation of the electrical activity. The position of the intravascular device within the blood vessel may be adjusted to more accurately determine the source of the electrical activity. Once the region of the patient's heart causing or involved with the arrhythmia is located, an ablation device may be introduced to ablate the tissue involved with or causing the arrhythmia and, thereby terminate the arrhythmia. For further details of intravascular devices for detecting electrical activity and for ablating or lysing tissue causing or involved with the electrical activity, reference is made to copending applications Ser. No. 08/188,619, filed on Jan. 27, 1994 now U.S. Pat. No. 5,509,411, Ser. No. 08/188,384, filed on Jan. 27, 1994, and Ser. No. 08/188,298, filed on Jan. 27, 1994, all of which are incorporated herein in their entireties. Preferably, the intravascular sensing device used to detect electrical activity also has means to ablate or otherwise lyse the tissue causing or involved with the electrical activity.

In one presently preferred embodiment of the invention, the catheter is provided with an inflatable balloon on its distal extremity to stop blood flow through the blood vessel in order to minimize misdirection of the contrast fluid and the dilution thereof which can interfere with fluoroscopic observation of the branch blood vessel.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a guiding catheter embodying features of the invention.

FIG. 2 is a transverse cross-sectional view of the catheter shown in FIG. 1 taken along the lines 2—2.

FIG. 4 is a partial elevational view, of an alternative embodiment wherein an occluding member is provided on the distal extremity of the catheter.

FIG. 5 is a transverse cross-sectional view of the catheter shown in FIG. 4 taken along the lines 5—5.

FIG. 6 is a transverse cross-sectional view of an alternative catheter shaft in which reinforcement is incorporated to provide a more torquable shaft.

FIG. 7 is a elevational view of a patient's coronary sinus with the catheter shown in FIG. 1 disposed within the coronary sinus with the balloon inflated to occlude the sinus and with the distal end of the catheter disposed within a branch vein leading to the sinus and with an intravascular device having sensing electrodes.

FIGS. 8–11 are schematic longitudinal cross sectional views of a variety of conventional shapes into which the distal extremity of the catheter may be formed.

DETAILED DESCRIPTION OF THE INVENTION

Figure 3:
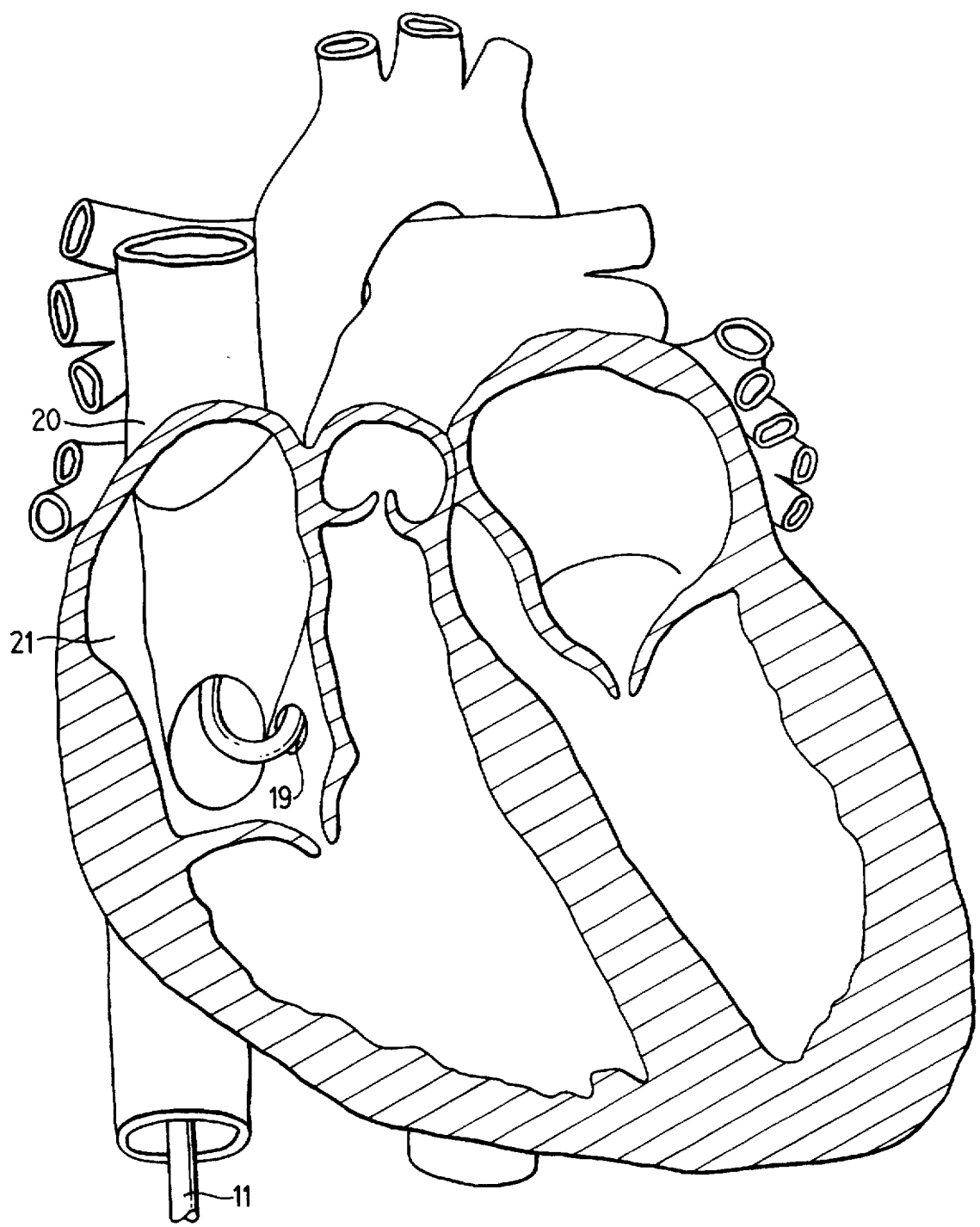
FIG. 3 is an elevational view of a patient's heart with portions of the heart wall removed to show the right atrium and coronary sinus ostium thereof.

As shown in FIGS. 1 and 2 the catheter 10 of the invention generally includes an elongated shaft 11, a distal shaft section 12, a proximal shaft section 13, an inner lumen 14 and an adapter 15 on the proximal end of the shaft 11. A port 16 is provided in the distal end of the catheter shaft 11 which

4 is in fluid communication with the inner lumen 14. The distal shaft section 12 includes a proximal portion 17 and a distal portion 18.

FIG. 3 illustrates the catheter 10 shown in FIG. 1 disposed within the patient's vascular system with the distal section 12 of the catheter seated within the patient's coronary sinus ostium 19. In this embodiment, the catheter 10 has been introduced from the femoral vein (not shown) and advanced through the superior vena cava 20 and into the right atrium 21.

An alternative embodiment of the invention is depicted in FIGS. 4 and 5. In this embodiment, the catheter 30 generally includes an elongated catheter shaft 31, a distal shaft section 32, a proximal shaft section 33, an inner lumen 34, a multiarm adapter 35 on the proximal end of the shaft 31 and an occlusion balloon 36 on the distal extremity of the shaft 31. A port 37 is provided in the distal end of the catheter shaft 31 which is in fluid communication with the inner lumen 34. The catheter shaft 31 is provided with an inflation lumen 40 which extends through the shaft 31 to the interior of the balloon 36 to direct inflation fluid therein. The side arm 41 of adapter 35 facilitates introduction of inflation fluid into the inflation lumen 40. The center arm 42 of the adapter 35 allows for the introduction of a guidewire or catheter or contrast fluid into the inner lumen 34.

FIG. 7 illustrates the distal extremity of the catheter 30 shown in FIGS. 4 and 5 disposed within a patient's coronary sinus 50 with the distal tip 51 thereof seated within a branch vein 52 leading to the coronary sinus and an intravascular device 70 for detecting electrical activity of a patient's heart extending from the lumen of the guiding catheter into the branch vein. As shown in FIG. 7, the intravascular device 70 generally includes a plurality of sensing electrodes 71 on the distal extremity of the device. The balloon 36 is shown in an inflated condition which occludes the passageway of the sinus 50. The balloon 36 may be formed of inelastic or elastic polymer materials. A presently preferred balloon, which is formed of polyurethane (Pellathane-80 A durometer), is available from World Medical of Miami, FL. Typically, the balloon has an I.D. of about 7F, and inflated diameter of about 8–13 mm and a length of about 9 mm.

An alternative embodiment is shown in FIG. 6 wherein the proximal portion of the catheter shaft 60 has braided reinforcement 61 to provide increased torquability. This embodiment may also have a first lumen 62 and a second inner lumen 63, which correspond to the inner lumens 34 and 40 respectively of the embodiment shown in FIGS. 4 and 5.

FIGS. 8–11 illustrate various conventional shapes for the distal extremity of the guiding catheter of the invention. The shape shown in FIG. 8 is commonly called a Josephson type curve, FIG. 9 represents a Damato type curve, FIG. 10 a El Gamal type curve and FIG. 11 a hockey stick type curve. The proximal, intermediate and distal shaft sections 13, 64 and 12 are as indicated. The proximal or distal portions of the distal shaft section may be shaped before insertion into the patient's body by heating the catheter with a mandrel of the desired shape disposed within the inner lumen of the distal extremity so that the distal extremity will keep the shape of the mandrel when the catheter is cooled. If desired, control lines (not shown) may be incorporated into the wall of the catheter and extend out the proximal end of the catheter shaft, whereby when tension is applied thereto after the catheter is inserted into the patient, the distal extremity of the catheter shaft is deflected or shaped in a desired manner. These drawings are provided with reference numbers as in FIGS. 1 and 2.

Although individual features of embodiments of the invention may be shown in some of the drawings and not in others, those skilled in the art will recognize that individual features of one embodiment of the invention can be combined with any or all the features of another embodiment. Various modifications and improvements may be made to the present invention without departing from the scope thereof.

What is claimed is:

1. A guiding catheter for directing an intravascular device within a patient's coronary sinus comprising:
   a) an elongated shaft having a proximal and distal ends, a port in the distal end and guidewire receiving lumen extending to and in fluid communication with the port in the distal end;
   b) a relatively stiff proximal shaft section of the elongated shaft;
   c) a relatively flexible distal shaft section of the elongated shaft having a length of about 2 to about 7 centimeters and being shaped with a bend to facilitate entry into the patient's coronary sinus;
   d) an expandable occluding member mounted on the flexible distal section; and
   e) an adapter on the proximal end of the elongated shaft to provide access to the quidewire receiving lumen extending within the elongated shaft.

2. The guiding catheter of claim 1 wherein the elongated shaft has an inflation lumen extending from the proximal end to a location spaced proximally from the distal end and the expandable occluding member is an inflatable balloon having an interior in fluid communication with the inflation lumen.

3. The guiding catheter of claim 1 wherein the distal section of the elongated shaft has a length of about 3 to about 6 centimeters.

4. The guiding catheter of claim 1 wherein the proximal shaft section is formed of a polymer material having a hardness of about 60 to about 85D (Shore).

5. The guiding catheter of claim 1 wherein the distal shaft section is formed of a polymer material having a hardness of about 80A to about 30D (Shore).

6. The guiding catheter of claim 1 including an intermediate section having a flexibility greater than the proximal shaft section and less than the distal shaft section.

7. The guiding catheter of claim 6 wherein the intermediate shaft section has a hardness of about 30 to about 60 (Shore).

8. The guiding catheter of claim 6 wherein the intermediate shaft section has a length of about 1 to about 8 centimeters.

9. The guiding catheter of claim 1 wherein the relatively flexible distal shaft section includes a proximal portion having a flexibility greater than that of the proximal shaft section, and a nontraumatic distal portion having a flexibility greater than that of the proximal portion, wherein at least one of the portions of the distal section is being shaped with a bend to facilitate entry within the patient's coronary sinus.

10. An intravascular assembly including
    a) a guiding catheter for directing an intravascular device within a patient's coronary sinus, comprising:
    an elongated shaft having a proximal and distal ends, a port in the distal end and a guidewire receiving lumen extending to and in fluid communication with the port in the distal end,
    a relatively stiff proximal shaft section of the elongated shaft,
    a relatively flexible distal section of the elongated shaft having a length of about 2 to about 7 centimeters and having a proximal portion having a flexibility greater than that of the proximal shaft section, and a nontraumatic distal portion having a flexibility greater than that of the proximal portion, wherein at least one of the portions of the distal section is being shaped with a bend to facilitate entry within the patient's coronary sinus;
    an expandable occluding member mounted on the flexible distal shaft section; and
    an adapter on the proximal end of the elongated shaft to provide access to the guidewire receiving lumen extending within the elongated shaft; and
    b) slidably disposed within the guidewire receiving lumen of the guiding catheter, an intravascular device for detecting electrical activity of a patient's heart from within a cardiac vein thereof which includes an elongated shaft, a plurality of sensing electrodes on a distal extremity of the intravascular device and individual electrical conductors electrically connected to the sensing electrodes.

11. The intravascular assembly of claim 10 wherein the intravascular device has a length greater than a length of the guiding catheter so that the proximal end of the intravascular device extends out the proximal end of the guiding catheter when the distal extremity of the intravascular device having sensing electrodes thereon extends out the distal end of the guiding catheter.

12. A method of detecting electrical activity within a patient's heart, comprising:
    a) providing a guiding catheter having
    an elongated shaft having a proximal and distal ends, a port in the distal end and guidewire receiving lumen extending to and in fluid communication with the port in the distal end,
    a relatively stiff proximal shaft section of the elongated shaft,
    a relatively flexible distal section of the elongated shaft having a length of about 2 to about 7 centimeters and having a proximal portion having a flexibility greater than that of the proximal shaft section, and a nontraumatic distal portion having a flexibility greater than that of the proximal portion, wherein at least one of the portions of the distal section is being shaped with a bend to facilitate entry within the patient's coronary sinus;
    an expandable occluding member mounted on the flexible distal shaft section; and
    an adapter on the proximal end of the elongated shaft to provide access to the guidewire receiving lumen extending within the elongated shaft;
    b) advancing the guiding catheter through the patient's peripheral venous system into a right atrium of the patient's heart;
    c) guiding the distal end of the guiding catheter through the coronary sinus ostium into the coronary sinus and into a branch vein which drains into the coronary sinus;
    d) advancing an intravascular device having sensing electrodes on a distal portion thereof through the guidewire receiving lumen of the guiding catheter under the distal portion of the intravascular device having sensing electrodes thereon extends out the port in the distal end of the guiding catheter; and
    e) detecting electrical activity by means of the sensing electrodes on the distal portion of the intravascular device.

13. The method of claim 12 including ablating heart tissue causing or involved with the sensed electrical activity.

14. The method of claim 14 further including the step of inflating the expandable occluding member before the detection of electrical activity.

15. A guiding catheter for directing an intravascular device within a patient's; coronary sinus, comprising:

a) an elongated shaft having proximal and distal ends, a port in the distal end and a guidewire receiving lumen extending to and in fluid communication with the port in the distal end;

b) a relatively stiff proximal shaft section of the elongated shaft, c) a relatively flexible distal section of the elongated shaft having a length of about 2 to about 7 centimeters and having a proximal portion having a flexibility greater than that of the proximal shaft section, and a nontraumatic distal portion having a flexibility greater than that of the proximal portion, wherein at least one of the portions of the distal section is being shaped with a bend to facilitate entry within the patient's coronary sinus;

d) an intermediate section of the elongated shaft having a flexibility greater than the proximal shaft section and less than the distal shaft section, and having an expandable occluding member; and e) an adapter on the proximal end of the elongated shaft to provide access to the guidewire receiving lumen extending within the elongated shaft.

16. The guiding catheter of claim 15 wherein the elongated shaft has an inflation lumen extending from the proximal end to a location spaced proximally form the distal end and the expandable occluding member is an inflatable balloon having an interior in fluid communication with the inflation lumen.

* * * * *